United States Patent [19]
Sankoorikal et al.

[11] 4,364,263
[45] Dec. 21, 1982

[54] HIGH PRESSURE LIQUID CHROMATOGRAPHIC SYSTEM

[75] Inventors: Varghese L. Sankoorikal; Keith D. Holmes, Jr., both of Greenville, N.C.

[73] Assignee: Burroughs Wellcome Co., Research Triangle Park, N.C.

[21] Appl. No.: 187,322

[22] Filed: Sep. 15, 1980

[51] Int. Cl.³ .......................................... G01N 31/08
[52] U.S. Cl. .............................. 73/61.1 C; 210/198.2
[58] Field of Search .................. 73/61.1 C; 210/198.2; 422/70

[56] References Cited

U.S. PATENT DOCUMENTS

| | | | |
|---|---|---|---|
| 3,373,872 | 3/1968 | Hrdina | 73/61.1 C X |
| 3,518,874 | 7/1970 | Hrdina | 73/61.1 C |
| 3,536,450 | 10/1970 | Dus et al. | 73/61.1 C X |
| 3,559,458 | 2/1971 | Hrdina | 73/61.1 C X |
| 3,676,649 | 7/1972 | Burk | 73/61.1 C X |
| 3,701,609 | 10/1972 | Bailey | 73/61.1 C X |
| 4,073,725 | 2/1978 | Takeuchi et al. | 210/198.2 X |
| 4,116,046 | 9/1978 | Stein | 73/61.1 C |

OTHER PUBLICATIONS

Ersser, R. S. et al., *Modular Apparatus for the Automation of Ion-Exchange Column Chromatographic Procedures*, In Laboratory Practice, vol. 24, No. 11, pp. 741-743, Nov. 1975.

*Primary Examiner*—Edward R. Kazenske
*Assistant Examiner*—Joseph W. Roskos
*Attorney, Agent, or Firm*—Donald Brown

[57] ABSTRACT

A high pressure liquid chromatograph system which includes a plurality of columns and a plurality of solvent containers (reservoirs) and which are selectable by use of a select or subsystem to permit the desired measurement (analysis) to be made by the system. With this system one may conveniently use a particular solvent system and a particular column to obtain a recording which is believed to be the most definitive by the user. Selection may conveniently be made by the user or by a microprocessor in accordance with predetermined program so that a completely automated overnight analysis of large numbers of different samples may be made.

5 Claims, 3 Drawing Figures

HIGH PRESSURE LIQUID CHROMATOGRAPHIC SYSTEM

BACKGROUND OF THE DISCLOSURE

This disclosure is directed to a new and improved system for use in making high pressure (or performance) liquid chromatograph instrument measurements and in particular to a system which permits the selection of at least one of a plurality of columns and at least one of a plurality of solvents at the option of the instrument user.

High pressure liquid chromatography is a well known procedure and conventionally is used in such areas as toxicology, clinical chemistry, criminology, food, petro chemicals, pharmacology and quality assurance.

Over the years there has developed the need for a low cost technique that would simply and automatically permit the selection of certain parameters such as solvent system and column type in the performance of high pressure liquid chromatographic measurements.

Experience has shown that depending upon the chemical components to be measured using HPLC, a specific type of packed column when used with a particular solvent system will produce a more satisfactory result than another combination of solvent system and column.

While one can conceivably accomplish the above by hand, this is not a particularly satisfactory or safe approach in a system such as HPLC where high pressures are involved. Accordingly a low cost system was needed to provide automatic selection of solvent and column in a manner that would be safe and would not result in possible system damage due to the high pressures involved. The present system provides a system that meets the above criteria. As used herein HPLC refers to high pressure or high performance liquid chromatography.

BRIEF DESCRIPTION OF THE DISCLOSURE

A high pressure liquid chromatograph system is disclosed which includes a plurality of columns and a plurality of solvent containers, means for providing an electrical signal to select a particular solvent container and a particular column, means responsive to said signal to move valves into position whereby a particular column of the system is coupled to receive a sample to be analyzed and the solvent in the solvent container selected.

More particularly low voltage signals are used to control the flow of air to step valves into position. The system also includes protection to shut down the system in the event of loss of power.

DETAILED DESCRIPTION OF THE INVENTION

Figure 1:
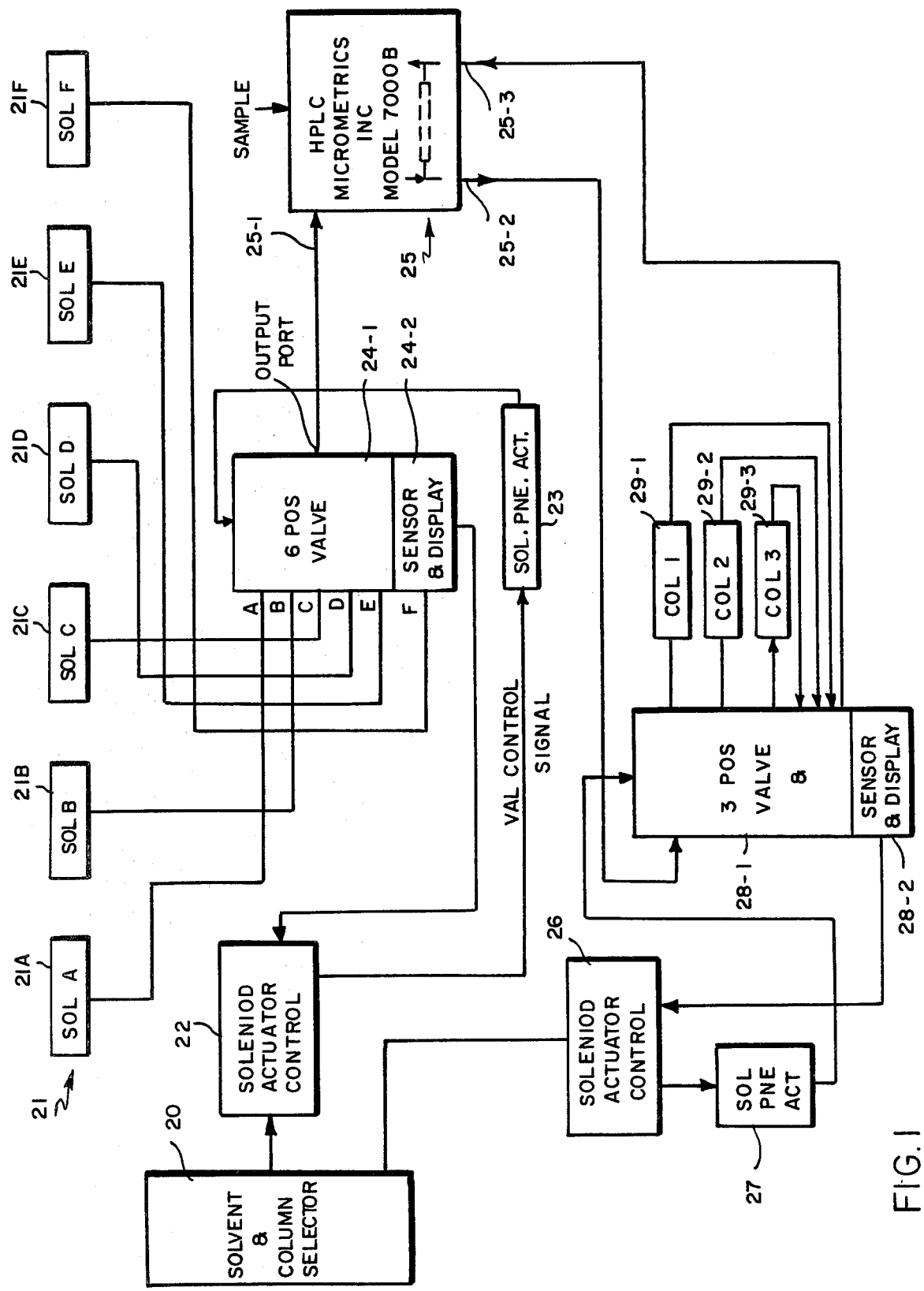
FIG. 1 is a block diagram of a solvent and column selector subsystem according to this disclosure.

FIG. 1 discloses in block diagram form the overall system of the invention which permits at least one of a plurality of solvents to be selected and fed into at least one of a plurality of high pressure columns with a sample to be analyzed. At 20 there is disclosed a selector which may comprise, as will be shown in more detail, switches to control solvent selection and switches to control column selection.

Alternatively to the use of switches a microprocessor or computer may provide the requisite signals for selection purposes. The solvents are each in solvent containers shown at 21-A, 21-B, 21-C, 21-D, 21-E and 21-F and may flow by gravity or by use of a pump as is well known in the art. Conventional solvents used in HPLC include methanol, water, acetonitrile, chloroform, toluene, etc., and are referred to as the "liquid phase". In order to control a six position solvent valve 24-1 there is provided a solenoid actuator control subsystem 22 which, based on the input selector signals, will move the valve 24-1 by way of controlling a solenoid pneumatic actuator 23.

At 26 there is shown a solenoid actuator control subsystem which provides a control signal to a solenoid pneumatic actuator 27 which controls a three position high pressure valve 28-1. One output port from valve 24-1 provides the selected solvent to one input port 25-1 of an HPLC device such as Model 7000B, U.S. Pat. No. 3,923,067, made by Micromeritics Instrument Corporation, Norcross, Georgia, U.S.A., or any other HPLC unit. In the Model 7000B system the standard HPLC pump system and the read out electronics are utilized and the HPLC column (shown dotted) internal to HPLC system (Micrometitics Inc. Model 7000B, U.S. Pat. No. 3,923,067) is bypassed and three separate columns shown at 29-1, 29-2 and 29-3 are utilized.

The input and output ports of the HPLC Model 7000B normally connected to its single column are directed to the three position valve 28-1 so that a sample and solvent may be provided to any of the selected columns 29-1, 29-2 or 29-3. At 24-2 there is shown a sensor and display which provides information relative to valve 24-1 position thereby indicating the solvent selected at any particular time and at 28-2 there is shown a sensor and display coupled to valve 28-1 for providing like information concerning column selection at any particular time.

The columns may each be filled (packed) with different materials, e.g., silica gel, octadecysilyl silica gel, a combination of both or other materials depending on the sample to be analyzed. The solvent selected is mixed with the sample as is conventional in HPLC Model 7000B and is provided under high pressure (1000 to about 5000 psi depending on preset conditions for the Model 7000B HPLC unit) and through output port 25-2 to the three position valve 26-1 and thence into one of the three columns selected to be separated into its chemical constituents.

The separated sample from the selected column is fed back through the valve to the HPLC input port 25-3 which is coupled to the ultra violet (UV) detector electronics of Model 7000B to provide information e.g., an absorbance spectrum which represents various components (compounds) in the sample. It should be understood that other detectors may also be used.

Figure 3:
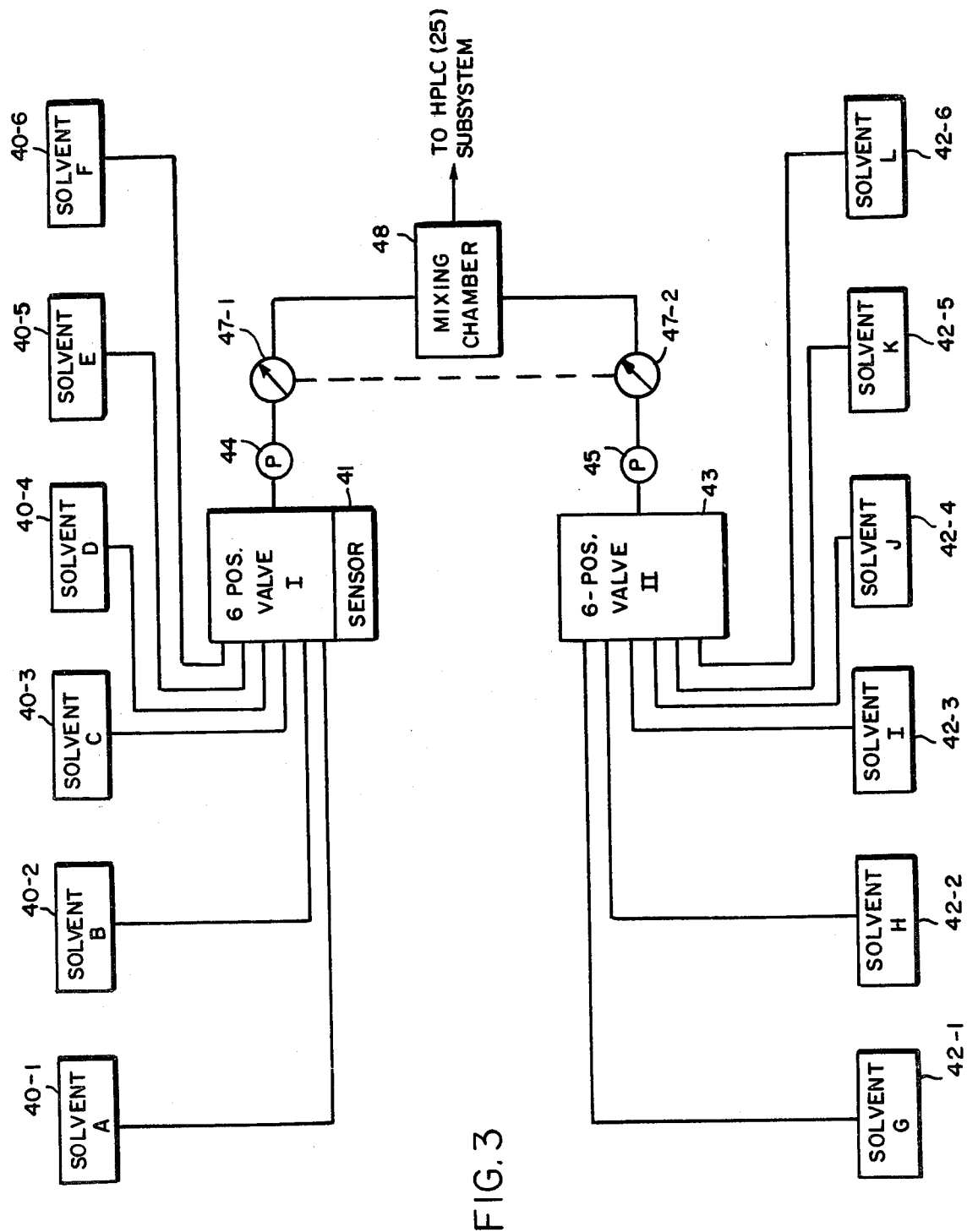
FIG. 3 is a block diagram of a modification to permit gradient operation by mixing of solvents.

It should be understood that this system may be modified by use of a plurality of multiple position valves as shown in FIG. 3 to feed more than one solvent and thereby mix solvents to permit the HPLC unit to be used in gradient mode whereby two solvents in equal or unequal amounts are mixed with a sample for passage through a column.

In the gradient mode a chromatogram better usable for detection identification, and quantitation purposes may be produced as is well known in the art depending upon the input sample.

While the system is particularly well suited to HPLC it can also be used whenever it is desired to switch a plurality of fluids and/or a plurality of separating devices which are coupled to a detector system.

Figure 2:
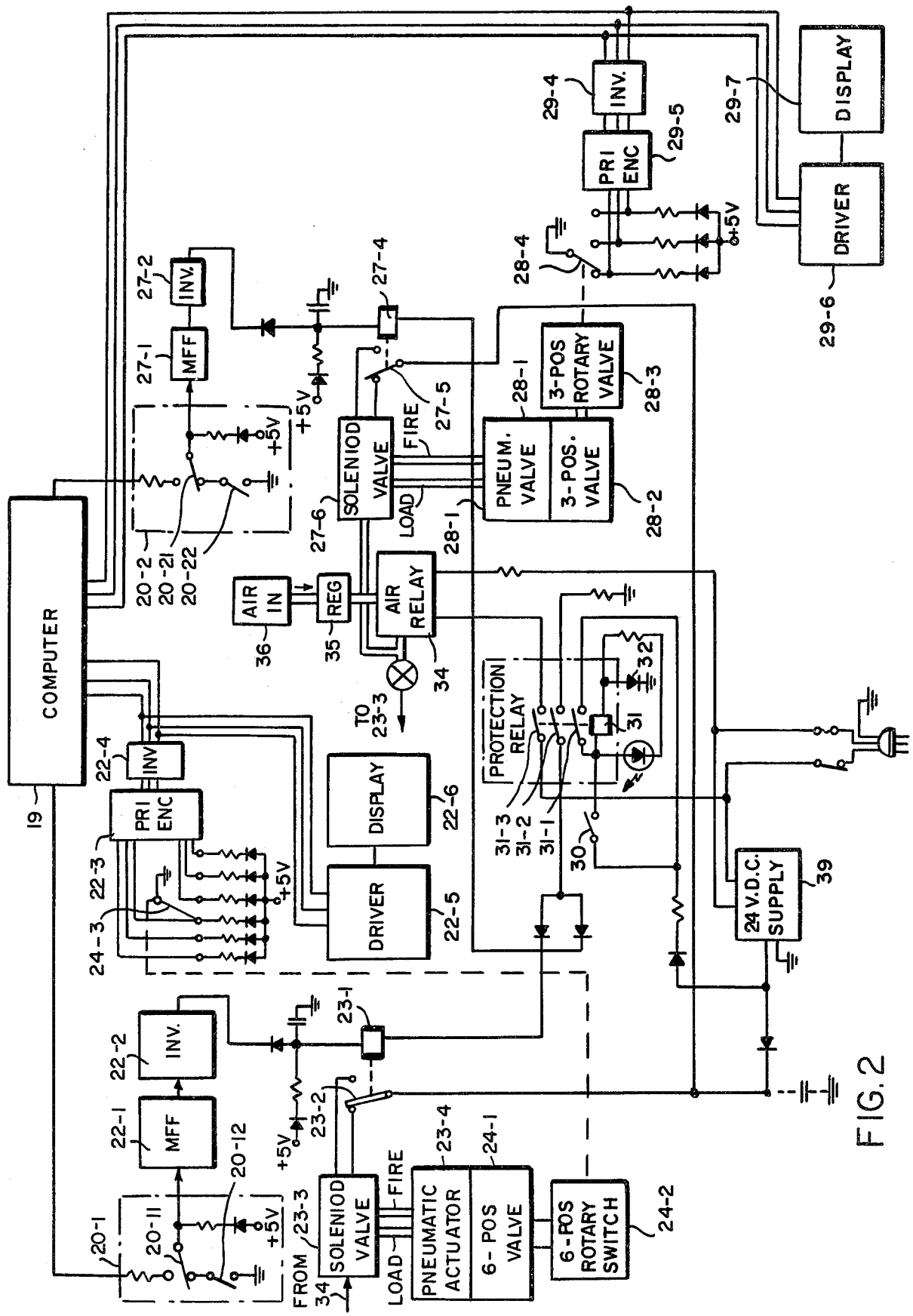
FIG. 2 is a detailed partial block diagram illustrating circuitry for operating the system of this disclosure.

Reference should now be had to FIG. 2 which discloses in more detail the electronics and pneumatics of the block diagram of FIG. 1. The selector block 20 of FIG. 1 is shown in FIG. 2 as two sections 20-1 and 20-2. Section 20-1 controls solvent selection i.e., selection of a particular solvent storage system having solvent therein and section 20-2 controls column selection.

The solvent section portion 20-1 comprises a switch 20-11 which is positionable on one of the two contacts so that column selection may be under computer e.g., microprocessor 19 control or to a switch 20-12 which may be operated by hand to generate an electrical signal to cause the generation of pulses by a one shot monostable multivibrator (MFF) 22-1. Each time switch 20-3 is closed (assuming sufficient time has elapsed so that the one shot monostable multivibrator (MFF) 22-1 has recovered), another pulse will be provided by the multivibrator 22-1 when the input thereto goes low as a result of switch 20-12 closure or a control signal is provided by computer 19.

Thus one shot multivibrator 22-1 provides a pulse upon each occurrence of a low input signal due to switch 20-12 causing the input to the one shot multivibrator 22-1 to go towards ground. The output of the one shot multivibrator 22-1 is provided to an inverter 22-2 which provides a low output signal to a solenoid 23-1. Solenoid 23-1 controls switch 23-2 which in turn controls a solenoid valve 23-3. The solenoid valve 23-3 operates a solenoid pneumatic valve actuator 23-4 whicch in turn controls a six position rotary pneumatic valve 24-1.

The rotary pneumatic valve 24-1 when under local control rotates one position for each opening and closing of the switch 20-12 i.e., each pulse from one shot multivibrator 22-1 causes the valve to move one position. Thus if solvent A is presently being provided to the input of the Model 7000B, Micromeritics, five closures of the switch 20-1 will produce five pulses that will cause solvent F to now be provided to the HPLC subsystem 25 (see FIG. 1).

In operation, a low signal from inverter 22-2 causes current to flow in solenoid coil 23-1 and move switch 23-2 coupled to +24 V from the load to the fire side of solenoid valve 23-3. The valve 23-3 may be a conventional solenoid valve which controls the flow of air under pressure from conventional air source subsystem i.e., air source 36, regulator 35 and air relay 34 to pneumatic actuator 23-4. In order to move the valve 24-1 from one position to another (one step) the actuator 23-4 must first be loaded with air and then fired. Not until air on the load side is vented will the actuator 23-4 cause the valve to move one position.

The rotary valve 24-1 may be a Type 50 (#5012) as sold by RHEODYNE INCORPORATED, Berkeley, California 94710, and the pneumatic actuator 23-4 may be #5003 as sold by RHEODYNE INCORPORATED.

Sensing the valve position and thus the solvent being dispensed is achieved by use of a six position rotary switch 24-2. The switch 24-2 has its wiper arm 24-2 grounded. When a specific contact is grounded it causes a selected input of a priority encode 22-3 (Ser. No. 74148N) to go low (it is normally at +5 V) and the output signal from the encoder is binary coded decimal (BCD) which represents valve position. The encoder BCD output is then fed to an inverter 22-4. The BCD output now high is displayed by way of a display driver 22-5 and a conventional common anode visual display module 22-6, comprising a conventional BCD to display segment generator and indicator lights. Obviously other types of BCD displays may be used as would be apparent to those skilled in the art. The BCD signal may also be provided to the computer e.g., microprocessor 19 which would use this information in determining how many pulses are needed to drive to the position desired.

The column selector portion 20-2 is provided with a switch 20-21 which is positionable on one of two contacts so column selection may be under computer 19 control or to a switch 20-22 which may be operated by hand to generate an electrical signal to cause the generation of pulses by a one shot monostable multivibrator (MFF) 27-1.

The one shot multivibrator 27-1 provides a pulse upon each occurrence of a low input signal due to switch 20-22 causing the input to the one shot multivibrator to go towards ground. The output of the one shot multivibrator 27-1 is provided to an inverter 27-2 which provides a low outpt signal to a solenoid 27-4. Solenoid 27-4 controls a switch 27-5 which in turn controls a solenoid valve 27-6. The solenoid valve 27-6 is coupled to air relay 34 and operates a valve pneumatic actuator 28-1 which in turn controls a 3 position, 8 port valve 28-2 e.g., part AH-CST-8-UHPa-N60, Valco Instrument Co., Houston, Texas.

The position of the valve 28-2 is displayed using a three position rotary switch 28-3 whose wiper arm 28-4 is coupled to ground. The contacts of switch 28-3 are coupled to a BCD priority encoder 29-5 (Ser. No. 74148N) which is in turn coupled to a display driver 29-6 via an inverter 29-4. The driver is coupled to a conventional common anode digital display 29-7 module comprising a conventional BCD to segment converter and display lights. The output of the inverter may also be coupled to the computer 19 so that the selection may be made under computer control.

In operation, the closure of normally open switch 20-22 (when the system is under local control) causes monostable multivibrator 27-1 to provide a pulse signal to cause solenoid 27-4 to move a contact 27-5 from the load to fire position. This causes the valve 27-6 to permit air from source 34 to step the 3 position 8 port valve 28 when actuator 28-1 is activated.

When column 29-1 is selected, the eight port valve permits solvent and sample to flow from HPLC Model 7000B (25) to column 29-1 input and back to HPLC through valve 28-2. The sample (as a plug) to be analyzed is injected into the solvent as is conventional by device 25.

The system herein includes a power system and power return surge protection. This is highly desirable in a chemical high pressure system such as this because the liquid sample in the HPLC column is normally at high pressure of up to 5000 psi. Without this protection, when the power returns after an interrupt, transient pulses spontaneously occur and but for this protection the valves would be moved to undesirable or partial positions which may produce erroneous results.

The power system has a protection relay system which operates as follows: when power is normally turned on, a normally open switch 30 is closed momentarily by user causing solenoid 31 to conduct through diode 32. This closes switches 31-1, 31-2, and 31-3 which in turn keeps solenoid 31 energized and permits air flow by air relay 34 and permits operation of solenoids 23-1 and 27-4 on the low voltage side. On a power interrupt, power is no longer available to solenoid 31 and switches 31-1, 31-2, 31-3, open thus preventing system operation until power returns and an operator momentarily recloses the normally open push button switch 30.

Reference should now be had to FIG. 3 which illustrates a scheme for using the present invention to mix solvents as desired for the unit 25.

In this embodiment a first set of six solvent containers 40-1, 40-2, 40-3, 40-4, 40-5 and 40-6 are coupled to a first solvent selector system 41 as disclosed with reference to FIGS. 1 and 2 and a second set of solvent containers 42-1, 42-2, 42-3, 42-4, 42-5 and 42-6 are coupled to a second solvent selector system 43 also as disclosed with reference to FIGS. 1 and 2. In order to combine the output from each selector subsystem in the amounts as desired there is provided pumps 44 and 45 whose output is coupled to ganged flow control valves 47-1 and 47-2 whereby the ratio of solvents from pumps 44 and 45 may be controlled.

Thereafter the solvents are combined in a mixing chamber 48 and thence feed on to HPLC subsystem 25.

While the foregoing has been disclosed with reference to particular hardware it is intended that this application is to cover use of different hardware as long as the same results are achieved.

We claim:

1. A high pressure liquid chromatographic system comprising a plurality of first means for providing a liquid phase, a plurality of columns, second means for receiving a sample to be analyzed and said liquid phase for transmission therefrom to said columns, first selector means coupled between said first means and said second means, said first selector means comprising means for producing electrical pulse signals, a first solenoid valve means and a first solenoid coupled thereto, said first solenoid valve means responsive to a signal which signal is selectively applied to said first solenoid valve means as a result of the presence or absence of an electrical pulse signal applied to said first solenoid, a source of air coupled to said first solenoid valve means, a first pneumatic actuator coupled to said first solenoid valve means and a multiple position valve coupled to said first actuator and between said first means and said second means, said pulse signals applied to the aforementioned first solenoid causing at least one of said first means to be selected to provide a liquid phase to said second means, second selector means coupled between said second means to receive the sample and liquid phase therefrom and permit it to be provided to a selected column, said second selector means comprising means for producing electrical pulse signals, second solenoid valve means and a second solenoid coupled thereto, said second solenoid valve means responsive to a signal which is selectively applied to said second solenoid valve means as a result of the presence or absence of an electrical pulse signal applied to said second solenoid, a source of air coupled to said second solenoid valve means, a second pneumatic actuator coupled to said second solenoid valve means and a multiple position valve coupled to said second actuator and between said columns and said first means, said pulse signals applied to the latter mentioned second solenoid selectively causing second means to be coupled to a selected one of said columns.

2. The system according to claim 1 in which said first and second selector means including means for indicating which first means is coupled to the second means at any particular point in time.

3. The system according to claim 1 in which said second means includes means coupled to the selected column to analyze the output from the column.

4. A high pressure liquid chromatographic system having at least one of a plurality of storage means to be selected for supplying a solvent and a plurality of column means to be selected comprising means for producing electrical pulses, solenoid means responsive to said pulses, a solenoid valve responsive to a voltage which is selectively applied thereto as a result of the presence or absence of a pulse being provided to said solenoid means, a source of air coupled to said solenoid valve, a pneumatic valve coupled to each of said plurality of means to be selected, and a pneumatic actuator coupled to said pneumatic valve for causing operation thereof and responsive to said solenoid valve controlling the flow of air thereto from said source of air.

5. A high pressure liquid chromatographic system comprising a plurality of storage means for storing solvent, a first multiple position valve coupled to each of said storage means, first means coupled to said first valve for combining a sample and a particular solvent from a particular one of said storage means depending upon the position of said first valve, a plurality of columns each having a top and bottom, a second multiple position valve coupled to said first means and the top and bottom of each of said columns, said second valve permitting the sample and solvent to enter the top of a particular one of said columns and permitting any remaining solvent and samples exiting from the bottom of the same column to be directed away from said same column.

* * * * *